United States Patent [19]

Dowling et al.

[11] Patent Number: 4,832,503

[45] Date of Patent: May 23, 1989

[54] STEAM QUALITY MONITORING MEANS AND METHOD

[75] Inventors: Donald J. Dowling; Jackie C. Sims, both of Houston, Tex.

[73] Assignee: Texaco Inc., White Plains, N.Y.

[21] Appl. No.: 115,319

[22] Filed: Nov. 2, 1987

[51] Int. Cl.[4] ..................... G01N 25/00; G01N 29/02
[52] U.S. Cl. ......................................... 374/42; 73/29; 374/135
[58] Field of Search ............... 374/42; 73/29, 24, 592, 73/861.04

[56] References Cited

U.S. PATENT DOCUMENTS

| | | | |
|---|---|---|---|
| 2,788,656 | 4/1957 | Sander | 73/24 |
| 3,192,516 | 6/1965 | Simpkins et al. | 73/592 X |
| 3,346,065 | 10/1967 | Bourguard | 73/24 X |
| 3,592,967 | 7/1971 | Harris | 73/592 X |
| 3,673,857 | 7/1972 | Teitelbaum | 73/592 X |
| 4,149,403 | 4/1979 | Muldary et al. | 73/29 |
| 4,193,290 | 3/1980 | Sustek, Jr. et al. | 73/29 |

Primary Examiner—Daniel M. Yasich
Attorney, Agent, or Firm—Robert A. Kulason; James J. O'Loughlin; Ronald G. Gillespie

[57] ABSTRACT

The present invention is an apparatus and method which monitors the quality of steam flowing in a pipe. A steam sensor located in the pipe provides a steam signal which is frequency related to the quality of the steam flowing in the pipe. A network connected to the sensor provides a high frequency signal and a low frequency signal in accordance with the steam signal. The steam quality is the in accordance with the high frequency signal and the low frequency signal.

8 Claims, 1 Drawing Sheet

U.S. Patent  May 23, 1989  4,832,503
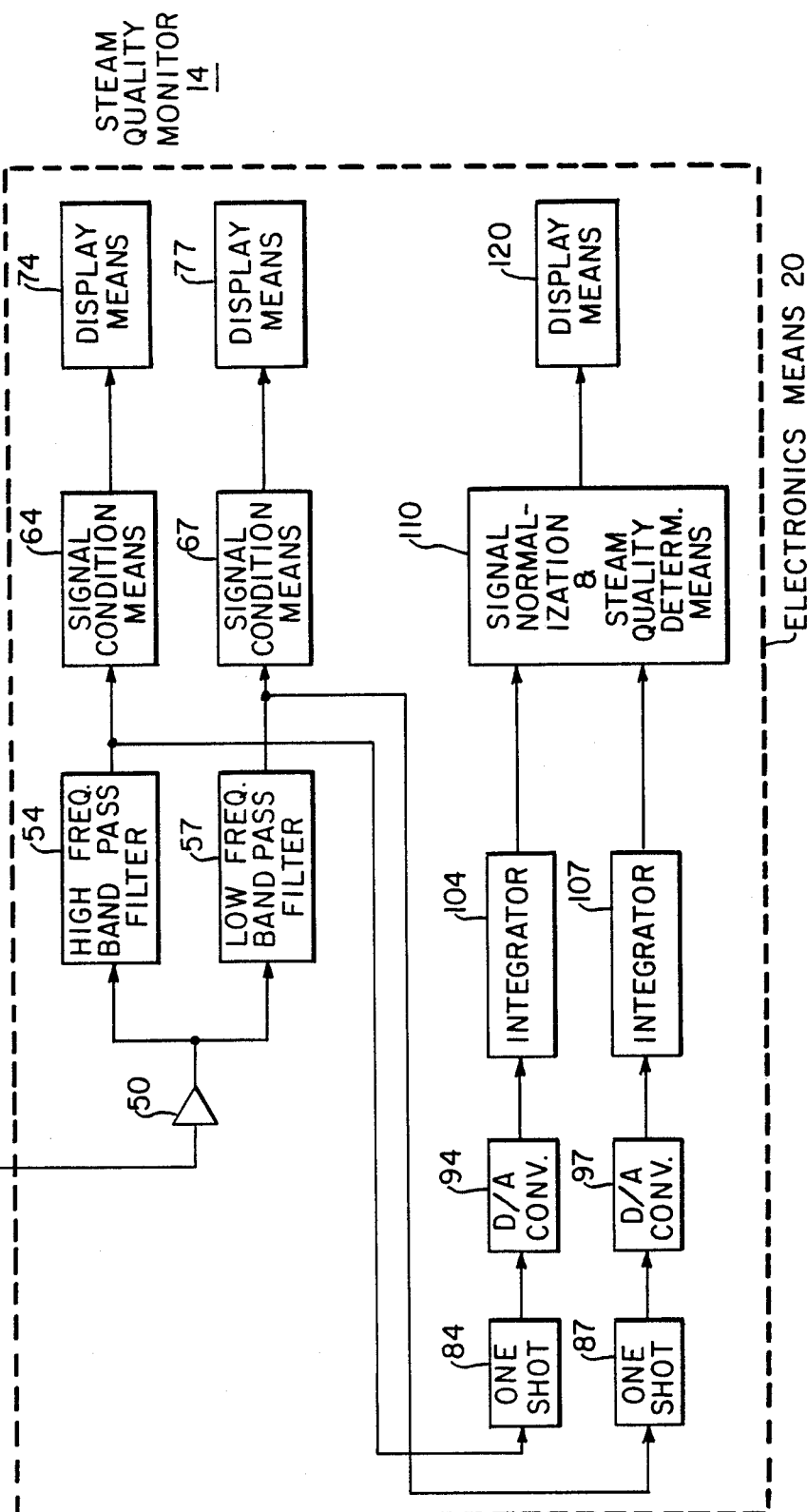

STEAM QUALITY MONITORING MEANS AND METHOD

BACKGROUND OF THE INVENTION

Field of the Invention

The present invention relates to steam monitors in general and, more particularly, to steam quality monitors.

SUMMARY OF THE INVENTION

The present invention is an apparatus and method which monitors the quality of steam flowing in a pipe. A steam sensor located in the pipe provides a steam signal which is frequency related to the quality of the steam flowing in the pipe. A network connected to the sensor provides a high frequency signal and a low frequency signal in accordance with the steam signal. The steam quality is monitored in accordance with the high frequency signal and the low frequency signal.

The objects and advantages of the invention will appear more fully hereinafter from a consideration of the detailed description which follows, taken together with the accompanying drawing wherein one embodiment of the invention is illustrated by way of example. It is to be expressly understood, however, that the drawings are for illustration purposes only and are not to be construed as defining the limits of the invention.

DESCRIPTION OF THE DRAWINGS

FIG. 1 is a simplified block diagram of a steam quality monitor shown in its relationship to the steam source and a well head.

FIG. 2 shows the steam monitor of FIG. 1 in greater detail.

DESCRIPTION OF THE INVENTION

Through the years many applications of steam power have made use of so-called dry steam or super-saturated steam. These terms refer to steam having negligible amounts of liquid water entrained in the flow and consequently can be treated as a single-phase flow of gas.

Instrumentation for monitoring single-phase gas flow has been available for some time, and while the technology for improving the accuracy and longevity of the instrumentation has improved, the actual difficulty of the measurement has not been too great.

In recent years there has been an increase in the use of steam where the "quality" is less than 100%. This two-phase flow regime consists of both dry steam and varying amounts of hot water together referred to as "wet steam".

In particular, enhanced oil recovery (EOR) operations on petroleum reservoirs are increasingly using steam flooding to improve the hydrocarbon sweep efficiency. However, it has been found that dry steam or super-saturated steam while transferring much heat might not provide the best overall treatment for a given field. One reason, for example, is that steam quality in the range of 80% provides more immunity to pipeline scale formation and plugging. Additionally, the economics of current EOR programs dictate the need for more accurate knowledge of the changing reservoir thermal characteristics. Economic considerations can suggest revisions in the amount of steam and hot water required as the production of the field changes. An accurate knowledge of the amount of steam and hot water being injected at any point in a reservoir is becoming increasingly important.

Applications of steam in an EOR field can be large and complex. A field consisting of many wells, a varying fraction of which may be steam injection wells or oil production wells, can be served by a multiplicity of steam generators, pipeline manifolds and hot water injection ports. It is not uncommon then, that two-phase steam flow prevails in the field and at varying qualities.

The measurements of two-phase gas/liquid flow has historically been a difficult task and frequently has resulted in inaccurate results. Conventional single-phase flow measurement techniques involving the use of orifice plates, venturi tubes etc., are usually found wanting when applied to two-phase gas/liquid flow having a wide range in quality.

Accordingly, a real need now exists for a means of providing inexpensive and accurate real-time steam quality information everywhere in a steam flood operation.

Some of the devices recently applied to this task use nuclear sources for measurement. Others obtain a side stream sample and separate it into liquid and vapor phases which are then measured separately. While there have been some successful applications of these types of devices, other techniques need consideration for the instrumentation of a field containing perhaps hundreds of wells.

Nuclear sources and their protective means numbering in the tens or hundreds per field can be an expensive solution to well head steam quality measurement. Likewise phase separation and measurement devices would be expensive in terms of investment and maintenance due to their complexity and if configured for portable use would preclude a complete data picture in real time of the entire injection program.

The present invention utilizes apparatus comparatively inexpensive enough for installation on each well head as desired.

Steam quality X is generally defined as the ratio of the mass, mg, of the steam vapor or gas to the sum of the mass, mg, of the gas and the mass, ml, of the liquid water present in the wet steam and can be expressed as $$X = (mg/mg + ml) \qquad (1)$$

In a flowing line containing wet steam equation (1) can be modified to take into account the slip velocity, s, which accounts for the different velocities exhibited by the gas and liquid phases. It of course would be necessary to know the values of these quantities to implement the relationship. Their determination while difficult in practice is not impossible.

However by locating the measuring apparatus in or near the exit of a nozzle, orifice or choke these difficult measurements can be avoided inasmuch as both phases are assumed to be traveling at the same velocity at that point. Negligible measurement error is introduced by this assumption.

It has been discovered that an acoustic transducer placed at a point such as the exit of a flowline choke or nozzle responds differently to the two phases of the wet steam. By selecting an acoustic transducer having suitable self-resonant frequency, the effects of the gas and liquid phases of the flow can be essentially separated. By means of spectrum analysis, preferential frequency bands which respond principally to the gas and liquid phases can be identified.

The present invention contemplates a means of determining the gas-liquid ratio in a two-phase gas-liquid flow regime by applying to the flow stream at or near the exit of a choke or nozzle an acoustic transducer whose output signal can be processed to provide an indication of the ratio of the gas and liquid present.

By applying suitable transducer and signal conversion constants to the transducer signal and/or with a calibration curve, the terms of (1) can be determined and the value of "X" determined.

With reference to FIG. 1, there is shown in very simplified form a steam source 3 providing steam to a well head 7 through a pipe 9 during an EOR operation. Obviously, as stated before, the steam source 3 may be applied through pipes to other well heads also. For simplicity of description only one well head is shown. As the steam passes through pipe 9, a steam quality monitor 14 monitors the quality of the steam. Steam quality monitor 14 is shown as having a dash line encompassing pipe 9. This is to signify that elements of steam quality monitor 14 are located within pipe 9. The signal from those elements is provided to electronics means 20.

With reference to FIG. 2, the steam quality monitor 14 is shown in more detail and includes a choke 24 located within pipe 9 which forces the steam into a narrow stream. Any device which constricts the flow of the steam may be used.

Positioned close to choke 24 within pipe 9 is a steam sensor means 27 which includes a protective deflector 32, an acoustic transducer 36, a mounting body 39, and support members 44. An electrical wire connected to transducer 36 passes out of pipe 9 through seal 48 and is connected to an impedance matching amplifier 50 in electronics means 20. Amplifier 50 provides a signal to a high frequency band pass filter 54 and to a low frequency band pass filter 57. One such high frequency band pass filter may pass frequencies in the 200 to 220 kHz band, while a low frequency band pass filter may pass frequencies in the 1 to 1.5 kHz.

While other frequency bands might be used, the wide separation in frequency between the bands listed, promotes band distinction and hence water/gas distinction.

Signal conditioning means 64 and 67 receive the signals from filters 54 and 57, respectively and condition them to display means 74 and 77, respectively, which may be digital readouts, analog meters or strip-chart recorders, empirically calibrated to show amounts of steam vapor and water volumes per unit time.

The signals from filters 54 and 57 are provided to one shot multivibrators 84 and 87, respectively. Each one shot multivibrator 84 or 87 provides a pulse signal output consisting of standard size pulses having the same frequency as the frequency of the signal provided to the one shot multivibrator. Obviously although the expression one shot multivibrator has been used any other circuit may be used that provides a pulse signal having standard size pulses and whose frequency is the same frequency as the signal from filter 54 or 57. The pulse signals from one shot multivibrators 84 and 87 are provided to digital to analog converters 94 and 97, respectively, where they are converted to analog signals and provided to integrators 104 and 107, respectively. The signals from integrators 104, 107 are provided to signal normalization and steam quality determining means 110 which determines quality in accordance with equation (1) and provides corresponding signals to display means 120.

What is claimed is:

1. Apparatus for monitoring the quality of steam flowing in a pipe, comprising:
   sensor means located in the pipe for providing a steam signal related to the quality of steam flowing in the pipe,
   filtering means, including a high frequency filter and a low frequency filter with each filter being connected to the sensor means, for filtering the steam signal to provide a high frequency signal and a low frequency signal, and
   monitoring means for monitoring the quality of the steam in accordance with the high frequency signal and the low frequency signal; and
   in which the sensor means includes:
   constriction means for constricting the flow of the steam in the pipe, and
   transducer means for providing the steam signal in accordance with the movement of the constricted steam past the transducer means.

2. Apparatus as described in claim 1 in which the filtering means includes:
   high frequency band pass filter means connected to the transducer means for passing high frequency components of the steam signal to provide the high frequency signal, and
   low frequency band pass filter means for passing low frequency components of the steam signal to provide the low frequency signal.

3. Apparatus as described in claim 2 in which the deriving means includes:
   first means for converting the high frequency signal to a signal whose amplitude corresponds to the frequency of the high frequency signal,
   second means for converting the low frequency signal to a signal whose amplitude corresponds to the frequency of the low frequency signal,
   first and second integrating means connected to the first and second frequency to voltage converting means for providing a pair of integrated signals, and
   means for determining the quality of the steam in accordance with the integrated signals and providing a signal corresponding thereto.

4. Apparatus as described in claim 3 in which each frequency to voltage converting means includes:
   a one shot multivibrator receiving either the high frequency signal or the low frequency signal and providing pulses having a pulse repetition rate corresponding to the frequency of the received signal, and
   digital to analog converter means for converting the pulses to the analog signal whose amplitude corresponds to the frequency of the received signal.

5. Apparatus as described in claim 4 in which the transducer means includes:
   an acoustical transducer responsive to the flow of steam past it to provide an electrical signal in accordance therewith,
   deflecting means mounted to the acoustical transducer in a manner so that it is between the acoustical transducer and the exit of the choke means for deflecting the steam past the transducer,
   means for mounting the transducer at a predetermined location within the pipe.

6. A method of monitoring the quality of steam flowing in a pipe, comprising the steps of:

providing a steam signal from a sensor related to the quality of steam flowing in the pipe, filtering the steam signal through a high frequency filter to privide a high frequency signal and through a low frequency filter to provide a low frequency signal, and monitoring the quality of the steam in accordance with the high frequency signal and the low frequency signal; and in which the steam signal providing step includes:

constricting the flow of the steam in the pipe with a device, and providing the steam signal in accordance with the movement of the constricted steam past the sensor.

7. A method as described in claim 6 in which the filtering step includes:

using high frequency band pass filter means connected to the sensor to pass the high frequency components of the steam signal so as to provide the high frequency signal, and using low frequency band pass filter means to pass low the frequency components of the steam signal so as to provide the low frequency signal.

8. A method as described in claim 7 in which the deriving step includes:

converting the high frequency signal to a converted signal whose amplitude corresponds to the frequency of the high frequency signal, converting the low frequency signal to a converted signal whose amplitude corresponds to the frequency of the low frequency signal, integrating the converted signals to provide a pair of integrated signals, determining the quality of the steam in accordance with the integrated signals, and providing a signal corresponding thereto.

* * * * *